US007262306B2

(12) United States Patent
Jenni et al.

(10) Patent No.: US 7,262,306 B2
(45) Date of Patent: Aug. 28, 2007

(54) CHEMILUMINESCENT COMPOUNDS AND THEIR USE

(75) Inventors: Wolfgang Jenni, Munich (DE); Dieter Heindl, Paehl (DE); Rupert Herrmann, Weilheim (DE); Hans-Peter Josel, Weilheim (DE); Gunter Lampert, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/326,852

(22) Filed: Jan. 6, 2006

(65) Prior Publication Data

US 2006/0199223 A1    Sep. 7, 2006

Related U.S. Application Data

(63) Continuation of application No. PCT/EP04/07426, filed on Jul. 7, 2004.

(30) Foreign Application Priority Data

Jul. 8, 2003    (EP)    ................... 03014587

(51) Int. Cl.
*C07D 209/56* (2006.01)
*G01N 33/53* (2006.01)
*C12Q 1/66* (2006.01)
*C07K 16/00* (2006.01)

(52) U.S. Cl. ........................... 548/427; 435/7.1; 435/8; 530/391.1

(58) Field of Classification Search ..................... None
See application file for complete search history.

(56) References Cited

U.S. PATENT DOCUMENTS

| 5,589,328 | A | 12/1996 | Manhant |
| 5,669,819 | A | 9/1997 | Mattingly et al. |
| 5,968,479 | A | 10/1999 | Ito et al. |

FOREIGN PATENT DOCUMENTS

| DE | 3645292 | 12/1997 |
| EP | 0257541 B1 | 3/1988 |
| EP | 0617288 B1 | 9/1994 |
| EP | 790238 B1 | 8/1997 |
| WO | WO95/19976 | 7/1995 |
| WO | WO98/56765 | 12/1998 |

OTHER PUBLICATIONS

Adamczyk, M. et al., "Modulation of the Chemiluminescent Signal from N¹⁰-(3-Sulfopropyl)-N-Sulfonylacridinium-9-Carboxamides," Tetrahedron 55(1999) 10899-10914.
Adamczyk, M. et al., "Neopentyl 3-Triflyoxypropanesulfonate. A Reactive Sulfopropylation Reagent for the Preparation of Chemiluminescent Labels," J. Org. Chem. 1998, 63, 5636-5639.
Dodeigne, C. et al., "Chemiluminescence as diagnostic tool. A review," Talanta 51 (2000) 415-439.
Flanagan, J. et al., "Functionalized Tricarbocyanine Dyes as Near-Infared Fluorescent Probes for Biomolecules," Bioconjugate Chem. 1997, 8, 751-756.
Hughes, D., "Progress in the Fischer Indole Reaction. A Review," Organic Preparations and Procedures Inr., 25 (6) 607-632 (1993).
Langer. P. et al., "Synthesis of Bis- and Tris(indolinylidenemethyl) benzenes by One-Opt Reactions of Polylithiated Nitriles with Bis(imidoyl)chlorides of Oxalic Acid," Eur. J. Org. Chem. 2002, 686-691.
Langer, P. et al., "Synthesis of Radialene-Shaped Pyrroles by Multiple-Anion-Capture Reactions of 1,3-Dianions," Chem. Eur. J. 2001, 7, No. 12, 2617-2627.
Mayer, A. et al., "Luminescent Labels-More than Just an Alternative to Radioisotopes?" Angewandte Chem. Intern Ed. ENgl. 33(1994) 1044-1072.
McCapra, F. et al., "Lumiescent Labels for Immunoassay—From Concept to Practice," Journal of Bioluminescence and Chemiluminescence vol , 51-58 (1989).
Moreno, I. et al., "A Simple Route to New Phenanthro- and Phenanthroid- Fused Thiazoles by a PIFA-Mediated (Hetero)biary Coupling Reaction," Eur. J. Org. Chem. 2002, 2126-2135.
Okajima, T. et al., "Chemiluminescence of indole and its derivatives induced by electrogenerated superoxide ion in acetonitrile solutions," Electrochimica Acta 47(2002) 1561-1565.
Soundararajan, S. et al., "Boronic Acids for Affinity Chromoatography: Spectral Methods for Determinations of Ionization and Diol-Binding Constants," Analytical Biochemistry 178, 125-134 (1989).
Tijssen, "Practice and Theory of Enzyme Immunoassays," (1990) Amsterdam, Elsevier.
Vetelino, M. et al., "A Mild Method for the Conversion of Activated Aryl Methyl Groups to Carboxaldehydes via the Uncatalyzed Periodate Cleavage of Enamines," Tetrahedron Letters, vol. 35, No. 2, 1994, 219-222.
Waldrop III, A. et al. "Chemiluminescent determination of hydrogen peroxide with 9-acridenecarbonylimidazole and use in measurement of glucose oxidase and alkaline phosphatase activity," Luminescence 2000; 15: 169-182.
Ximenes, V. et al., "The Oxidation of Indole Derivatives Catalyzed by Horseradish Peroxidase is Highly Chemiluminescent," Archives of Biochemistry and Biophysics, vol. 387, No. 2, Mar. 15, 2001, 173-179.
Zimmermann, T., "Ring Transformations of Heterocyclic Compounds, XXI(1)_. Diastereoselective Built-up of an Aroylcyclohexadiene Moiety as Second Spiro-connected Ring at Spiroindolines by Pyrylium Ring Transformation," J. Heterocyclic Chem., 39, 255-262(2002).

*Primary Examiner*—Cecilia J. Tsang
*Assistant Examiner*—Robert Havlin
(74) *Attorney, Agent, or Firm*—Marilyn L. Amick; Roche Diagnostics Operations, Inc.

(57) ABSTRACT

The present invention relates to novel chemiluminescent compounds, to a method for synthesizing these compounds, to derivatives and conjugates comprising these compounds, to the use of these compounds or conjugates thereof in chemiluminescence based assays, especially in immunoassays.

7 Claims, 5 Drawing Sheets

"dark reaction"  "chemiluminescence/ light reaction"

A⁻ = counterion
Z = leaving group

"dark reaction"   " chemiluminescence/ light reaction"

CHEMILUMINESCENT COMPOUNDS AND THEIR USE

RELATED APPLICATIONS

This application is a continuation of PCT/EP2004/007426 filed Jul. 7, 2004, which claims priority to EP 03014587.4 filed Jul. 8, 2003.

FIELD OF THE INVENTION

The present invention relates to novel chemiluminescent compounds of general Formula I:

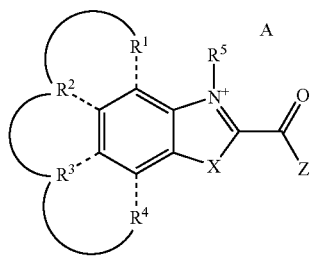

wherein at least one of $R^1$ and $R^2$, $R^2$ and $R^3$ or $R^3$ and $R^4$ are part of a fused aryl ring, each of which is optionally substituted one, two or three times with R, halogen, —$NR_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR or —S(O)$_2$NH$_2$ and any residues of $R^1$ to $R^4$ which are not part of a fused aryl ring independently represent hydrogen, R, halogen, —$NR_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR or —S(O)$_2$NH$_2$;

R5 represents alkyl, alkenyl, alkynyl or aralkyl wherein said alkyl, alkenyl or alkynyl can contain up to 20 heteroatoms, and may also contain a coupling moiety;

X represents —$CR^6R^7$—, —O—, —S— or —$NR^6$—, wherein $R^6$ and $R^7$ are independently defined as $R^5$ above; or $R^6$ and $R^7$ in —$CR^6R^7$— form, together with the carbon atom to which —they are attached, an cyclohexyl ring;

R represents alkyl, alkenyl, alkynyl or aralkyl wherein said alkyl, alkenyl or alkynyl can contain up to 20 heteroatoms;

Z represents a leaving group; and

A, if required, represents a counter-ion to balance a net charge of the compound.

The invention also relates to a method for synthesizing the compounds of Formula I, to derivatives and conjugates comprising these compounds, to the use of these compounds or conjugates thereof in chemiluminescence based assays, especially in immunoassays.

BACKGROUND OF THE INVENTION

The specific detection and quantification of biological molecules has been accomplished with excellent sensitivity for example by the use of radio-labeled reporter molecules. The first radio immunoassays developed in the end of the 1950's have matured into the most important tools of in vitro diagnostics, especially in medicine, using a broad variety of different detection or reporter systems. Well-known examples of reporter molecules are enzymes, labeled latex beads, fluorescent dyes and especially chemiluminescent dyes.

Reviews describing the theory and practice of specific binding assays are available. The skilled artisan will find all necessary technical details for performing specific binding assays in textbooks like Tijssen, "Practice and theory of enzyme immunoassays" (1990) Amsterdam, Elsevier and various editions of Colowick, S. P., and Caplan, N. O., Methods in Enzymology (1980-1986), Academic Press, dealing with immunological detection methods, especially volumes 70, 73, 74, 84, 92 and 121.

Paralleled by the development of light measuring techniques and the commercial availability of highly sensitive apparatuses, luminophores have in many applications replaced isotopic labels. Some of the new luminescent labels facilitate analyte detection at extremely low levels of sensitivity. Therefore such labels also commercially are very interesting.

Luminescent labels may be subdivided into the group of fluorescent labels and the group of luminescent labels. Whereas fluorescent labels require irradiation of a sample with excitation light in order to detect and measure the fluorescent label present, the luminescent systems, e.g., chemiluminescent systems do not require an extra source of light.

A widely used class of chemiluminescent labels are the acridinium compounds. Their mechanism of chemiluminescence has been extensively studied and is nicely summarized in a review article published by Mayer, A., and Neuenhofer, S., Angewandte Chem. Intern. Ed. Engl. 33 (1994) 1044-1072, Weinheim, VCH Verlagsgesellschaft mbH, as well as in a review article by Dodeigne, C., et al., Talanta (2000) 415-438.

Several mechanisms leading to emission of light according to the chemiluminescence principles have been proposed. Short-lived intermediates are considered part of the processes leading to decarboxylation and emission of light. The processes postulated for acridinium ester labels, resulting in emission of light or in the unwanted side reaction (dark reaction) leading to hydrolysis of the ester, are schematically shown in FIG. 1.

According to the proposed mechanism the carbonyl group (which has been part of the amide or ester bond) by attack of $H_2O_2$ becomes part of a dioxetanone moiety. Spontaneous decomposition of the dioxetanone moiety is accompanied by light emission and yields a heterocyclic ketone and $CO_2$ in case of a carbonyl group, or in more general chemical terms a heterocumulene in case functional equivalents of the carbonyl group had been present.

It is instantly evident from FIG. 1, that the light reaction (LR) and the dark processes (DP) both are dependent on the properties of the leaving group Z.

An essential feature of the acridinium esters used in diagnostic applications is that the ester function has been substituted to carry a suitable leaving group Z. Suitable leaving groups are designed to match as good as possible two essential requirements: stability and high quantum yield.

On the one hand the leaving group of an acridinium esters must be as active as possible, i.e., leaving quite readily under measurement conditions, to allow for a sensitive detection and high quantum yield. This high activity on the other hand, however, goes to the expense of instability towards hydrolysis. Such instabilities are even more critical if such chemiluminescent labels are used for conjugation to biomolecules. The goal to achieve a high chemiluminescence yield and in addition a high stability of the labeled reagent equals to a fine balance act always ending in a compromise between light yield and stability.

To at least partially reduce the problems encountered, new and different leaving groups have been designed and proposed.

EP 617 288 gives examples of appropriate leaving groups. Most popular are N-sulfonamides, e.g., described in U.S. Pat. No. 5,669,819, thioesters as described in DE 3 645 292, hydroxamic acid esters described in WO 98/56765, imidazolides as described by Waldrop III, A. A., et al., Luminescence 15 (2000) 169-182, and pyridinium amides (WO 95/19976).

Besides the acridinium labels, other well known chemiluminescence based systems make use of labels comprising amongst others the following categories, the combination of luciferins with corresponding luciferases, cyclic arylhydrazides, acridinium derivatives, stable dioxetanes, and oxalic acid derivatives.

However, overall only a rather limited number of chemiluminescent basic compounds is known and even less have proven useful for routine diagnostic applications.

It was the task of the present invention to find and identify a novel class of compounds appropriate for chemiluminescence assays which compounds provide for a stable chemiluminescent dye or label on the one hand and for sensitive detection or high quantum yield on the other hand. Such compounds additionally should be suitable for labeling of, or conjugation to a biomolecule, e.g., a specific binding partner. I.e., it should be possible to introduce a coupling group without impairing the chemiluminescence properties of such compounds and/or the compound itself should not interfere with the biomolecule.

SUMMARY OF THE INVENTION

It has been found that the compounds of Formula I are chemiluminescent. Since the compounds according to the present invention encompass both storage stability, as well as sensitive detection in chemiluminescent procedures they are also used to label biomolecules and the resulting conjugates with great advantage can be applied in appropriate specific binding assays for detection of an analyte in a sample.

DETAILED DESCRIPTION OF THE INVENTION

Figure 1:
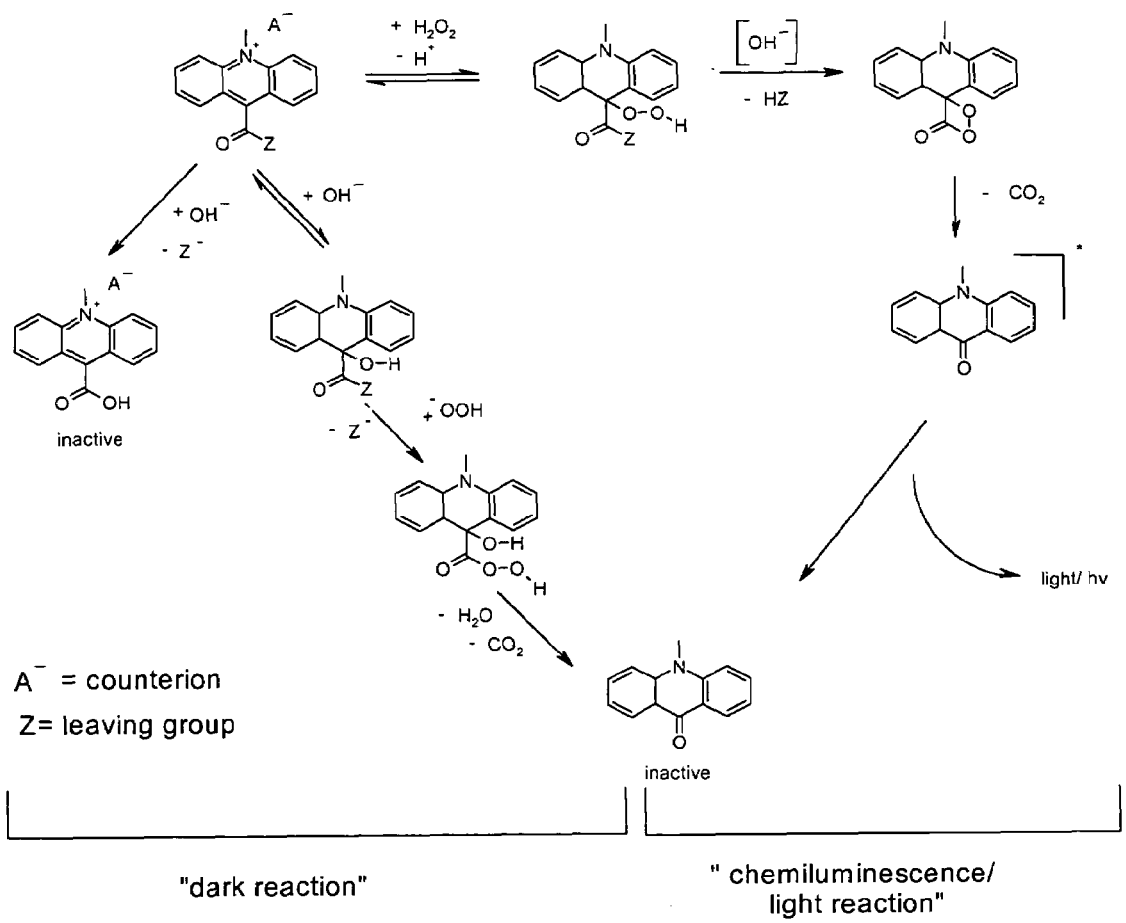
FIG. 1: Acridinium labels Shown are postulated reaction mechanisms leading to chemiluminescence or non-luminescent decay. Both possible pathways are depicted. The light creating reaction, or light reaction (=LR) leads to chemiluminescence, whereas the dark reaction pathway, or dark process (DP) leads to direct hydrolysis not accompanied by light emission.

In a first embodiment the present invention relates to a compound of Formula I:

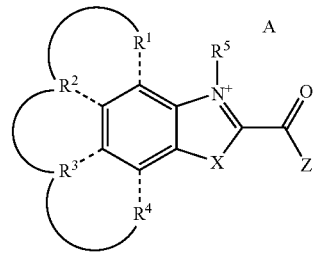

wherein at least one of $R^1$ and $R^2$, $R^2$ and $R^3$ or $R^3$ and $R^4$ are part of a fused aryl ring, each of which is optionally substituted one, two or three times with R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR or —S(O)$_2$NH$_2$ and any residues of $R^1$ to $R^4$ which are not part of a fused aryl ring independently represent hydrogen, R, halogen, —NR$_2$, —OR, —OH, —S(O)$_2$OH, —CN, —SCN, —SSR, —SR, —C(O)R, —C(O)H, —C(O)OR, —C(O)OH, —NHC(O)R, —C(O)NHR, —C(O)NH$_2$, —S(O)$_2$NHR or —S(O)$_2$NH$_2$;

$R^5$ represents alkyl, alkenyl, alkynyl or aralkyl wherein said alkyl, alkenyl or alkynyl can contain up to 20 heteroatoms, and may also contain a coupling moiety;

X represents —CR$^6$R$^7$—, —O—, —S— or —NR$^6$—, wherein R$^6$ and R$^7$ are independently defined as R$^5$ above; or R$^6$ and R$^7$ in —CR$^6$R$^7$— form, together with the carbon atom to which they are attached, an cyclohexyl ring;

R represents alkyl, alkenyl, alkynyl or aralkyl wherein said alkyl, alkenyl or alkynyl can contain up to 20 heteroatoms;

Z represents a leaving group; and

A, if required, represents a counter-ion to balance a net charge of the compound.

Preferably only one of $R^1$ and $R^2$, $R^2$ and $R^3$ or $R^3$ and $R^4$ are part of an fused aryl ring.

More preferably only one of $R^1$ and $R^2$ or $R^3$ and $R^4$ are part of an fused aryl ring, especially only $R^3$ and $R^4$ are part of an fused aryl ring.

Preferably the optional substituents on said fused aryl ring are fluorine, chlorine, —OH, —C(O)CH$_3$, —S(O)$_2$OH, —S(O)$_2$NH$_2$ or —S(O)$_2$NHR, wherein R is defined as above. Preferably said substituents are fluorine, chlorine, —OH, —C(O)CH$_3$, —S(O)$_2$OH or —S(O)$_2$NH$_2$, especially fluorine, chlorine, —OH or —C(O)CH$_3$.

Preferably any residues of $R^1$ to $R^4$ which are not part of an fused aryl ring independently represent hydrogen, fluorine, chlorine, —OH, —C(O)CH₃, —S(O)₂OH, —S(O)₂NH₂ or —S(O)₂NHR, wherein R is defined as above. More preferred any residues of R¹ to R⁴ which are not part of an fused aryl ring independently represent hydrogen fluorine, chlorine, —OH, —C(O)CH₃, —S(O)₂OH or —S(O)₂NH₂, especially fluorine, chlorine, —OH or —C(O)CH₃.

The group R⁵ preferably is selected from alkyl, sulfoalkyl or alkylamidoalkyl.

The group R⁵ is further on preferably selected from alkyl or sulfoalkyl.

More preferred R⁵ is selected from methyl, ethyl, sulfopropyl and sulfobutyl.

Optionally R⁵ also comprises a coupling moiety capable of attaching the compound to a protein, a nucleic acid or a specific binding material. Preferably said coupling moiety is selected from the group consisting of N-succinimidyl-oxycarbonyl, maleinimido, 4,6-dichloro-[1,3,5]triazin-2-amino-, N-benzotriazolyl-oxycarbonyl, N-phtalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —SO₂Cl, —SO₂Br, —SO₂I, —NH₂, —N₃, —N=C=O, —N=C=S, —N₂⁺, —Cl, —Br or —I.

Further preferred the coupling moiety is selected from the group consisting of N-succinimidyl-oxycarbonyl, N-benzotriazolyl-oxycarbonyl, maleinimido, N-phtalimidyl-oxycarbonyl, aryloxycarbonyl as e.g. p-nitrophenyloxycarbonyl or pentafluorophenyloxycarbonyl, imidate, p-aminobenzoyl, —C(O)Cl, —C(O)Br, —SO₂Cl, —NH₂, —N₃. More preferred the coupling moiety is a N-succinimidyl-oxycarbonyl group or —SO₂Cl. Especially preferred the coupling moiety is a N-succinimidyl-oxycarbonyl.

Preferably X is selected from the group consisting of —CR⁶R⁷—, —O—, and —S—, wherein R⁶ and R⁷ are as defined above.

More preferred X is —CR⁶, R⁷— with R⁶ and R⁷ as defined above.

Preferably R⁶ and R⁷ independently represent methyl or ethyl.

In one embodiment of the invention X is —CR⁶,R⁷— with R⁶ and R⁷ independently representing alkyl.

In another embodiment of the invention X is —CR⁶,R⁷— with R⁶ and R⁷ forming, together with the carbon atom to which they are attached, an cyclohexyl ring.

As defined above R⁶ or R⁷ can also comprise a coupling moiety capable of attaching the compound to a protein, a nucleic acid or a specific binding material. Said coupling moiety is defined as the optional coupling moiety in R⁵ above.

The counterion A, if representing an anion is preferably selected from the group consisting of halide, CH₃SO₄⁻, CF₃SO₃⁻, FSO₃⁻, C₄F₉SO₃⁻, or CH₃C₆H₄SO₃⁻.

If A represents an cation, it is preferably selected from the group consisting of K⁺, Na⁺, tetraalkylammonium.

The leaving group Z is selected from —O—V, —S—V, —N(V)—SO₂—V', —O—N(V)—SO₂—V', —S—N(V)—V', —O—N(V)—C(O)—V', —O—N=C(V)—V' or —O—N=C(V)—Cl, wherein V or V' independently represent alkyl, which is optionally substituted 1 or 2 times by —S(O)₂OH or 1 to 5 times by fluorine or chlorine, preferably fluorine; and/or V or V' independently represent an aryl moiety corresponding to the following formula

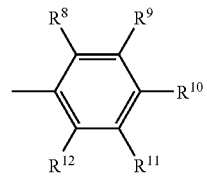

wherein R⁸ and R¹² independently represent hydrogen, halogen, alkyl, alkenyl, alkynyl, alkoxy, alkylsulfanyl or alkylamido, R⁹ and R¹¹ are defined as above R¹ to R⁴, which are not part of a fused aryl ring, R¹⁰ represents —R¹³—R¹⁴, wherein R¹³, if present, represents alkyl, alkenyl, alkynyl or alkylamido wherein said alkyl, alkenyl or alkynyl can contain up to 20 heteroatoms, or R¹³, if present, represents an electron-withdrawing group, and R¹⁴, if present, represents a coupling moiety which is defined as above the coupling moiety optionally comprised in R⁵. As the skilled artisan will appreciate, such a coupling moiety is present only once in either R⁵, R⁶, R⁷ or R¹⁰.

R⁹ and R¹⁰, and R¹¹ and R¹⁰ are interchangeable.

The electron-withdrawing group present in R¹³ preferably is selected from —NO₂, —CN, —Cl or —N⁺(CH₃)₃, alkylcarbonyl, or alkoxycarbonyl, wherein the alkyl or the alkoxy part is optionally substituted once by aryl.

Preferably Z represents —O—V, —S—V or —NV—SO₂—V' and especially preferred Z represents —O—V or —NV—SO₂—V'.

The pKa-value of the leaving group Z is among other aspects essential for the chemiluminescence quantum yield on the one hand and for the stability against hydrolysis on the other hand (McCapra, F., et al., J. Biolumin. Chemilumin. 4 (1989) 51-58 ; Adamczyk, M., et al., Tetrahedron 55 (1999) 10899-10914). To meet these requirements, the pKa-value of the leaving group Z is preferably between 5.0 and 12.5. The corresponding pKa-value can be determined by the method of Soundararajan, S., et al., Anal. Biochem. 178 (1989) 125-134. More preferred the leaving group Z has a pKa-value between 6.0 and 12.0.

The term "wherein said alkyl, alkenyl or alkynyl can contain up to 20 heteroatoms" refers to the corresponding foresaid alkyl, alkenyl or alkynyl groups. It means that said alkyl, alkenyl or alkynyl groups are optionally interrupted one to five times by —O—, —N(CH₃)—, —S—, —S(O)₂—, —S(O)₂O—, —OS(O)₂—, —S(O)₂NH—, —NHS(O)₂—, —C(O)—, —OC(O), —C(O)O—, —NHC(O)— or —C(O)NH—, and said alkyl, alkenyl or alkynyl groups are optionally substituted one to five times with —S(O)₂OH, —OH, —C(O)OH, fluorine or chlorine such that not more than 20 heteroatoms, preferably not more than 15 heteroatoms, also preferably not more than 10 heteroatoms, are comprised in said alkyl, alkenyl or alkynyl groups. Preferably said alkyl, alkenyl or alkynyl groups are optionally interrupted by —O—, —NHC(O)— or —C(O)NH—, and said aliphatic hydrocarbon groups are optionally substituted by —S(O)₂OH, —OH, —C(O)OH.

The term "alkyl" denotes a straight-chain or branched saturated hydrocarbon group having 1 to 20, preferably 1 to 10, more preferred 1 to 5 carbon atoms. Examples of the "alkyl groups" include C1-20 alkyl groups, more preferred C1-10 alkyl groups such as methyl, ethyl, propyl, isopropyl, butyl, isobutyl, sec.-butyl, tert.-butyl, pentyl, isopentyl, neopentyl, tert.-pentyl, hexyl, isohexyl, heptyl, octyl, nonyl, decyl, 1,1-dimethylbutyl, 2,2-dimethylbutyl, 3,3-dimethylbutyl and 2-ethylbutyl.

The term "alkenyl" denotes an unsaturated straight-chain or branched aliphatic hydrocarbon group containing one double bond and having 2 to 20, preferably 2 to 10, more preferred 1 to 5 carbon atoms. Examples of the "alkenyl group" include C2-20 alkenyl groups, more preferred C2-10 alkenyl groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" denotes an unsaturated straight-chain or branched aliphatic hydrocarbon group containing one triple bond and having 2 to 20, preferably 2 to 10, more preferred 1 to 5 carbon atoms. Examples of the "alkynyl group" include C2-20 alkynyl groups, more preferred C2-10 alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "alkoxy" as used herein means an alkyl group as defined above, which is attached via an oxygen-atom.

The term "alkylsulfanyl" as used herein means an alkyl group as defined above, which is attached via an sulfur-atom.

The term "alkylamido" as used herein means an alkyl group as defined above, which is attached via —C(O)NH— or —NHC(O)—.

The term "sulfoalkyl" as used herein means an alkyl group as defined above, which is substituted by —SO$_3$H.

The term "alkylamidoalkyl" means an alkyl group as defined above, which is interrupted once by —C(O)NH— or —NHC(O)—

The term "alkylcarbonyl-oxycarbonyl" means an alkyl group as defined above, which is attached via —C(O)OC(O)— and which is optionally substituted one or several times by —NO$_2$, halogen or —N$^+$(CH$_3$)$_3$.

The term "alkoxycarbonyl" means an alkyl group as defined above, which is attached via —OC(O)— and which is optionally substituted one or several times by —NO$_2$, halogen or —N$^+$(CH$_3$)$_3$.

The term "aryl" denotes a monocyclic or a condensed polycyclic aromatic hydrocarbon group, preferably exemplified by C6-14 aryl groups such as phenyl, naphthyl, anthryl, phenanthryl and 9-fluorenone-2-yl, especially monocyclic or condensed bicyclic aromatic hydrocarbon groups such as phenyl, 1-naphthyl and 2-naphthyl. Preferably aryl means a phenyl moiety.

The term "aralkyl" as used herein denotes an aryl group as defined above attached to a straight chain or branched alkylene group having 1 to 15, preferably 1 to 10, more preferred 1 to 5 carbon atoms,. Example of such groups are benzyl, 1-phenethyl, 2-phenethyl as well as phenpropyl and phenbutyl together with their isomers.

The term "arylcarbonyl-oxycarbonyl" means an aryl group as defined above, which is attached via —C(O)OC(O)— and which is optionally substituted one or several times by —NO$_2$, —CN, halogen, —C(O)CH$_3$ or —N$^+$(CH$_3$)$_3$.

The term "aryloxycarbonyl" means an aryl group as defined above, which is attached via —OC(O)— and which is optionally substituted one or several times by —NO$_2$, —CN, halogen, —C(O)CH$_3$ or —N$^+$(CH$_3$)$_3$.

The term "halogen" means fluorine, chlorine, bromine and iodine, especially fluorine, chlorine and bromine.

The term "imidate" means an alkyl group or an aryl group as defined above, which is attached via —OC(=NH)—.

The compounds of the general Formula I may be prepared by any process known to be applicable for the preparation of chemically-related compounds by the one skilled in the art. Such processes, when used to prepare the compounds of Formula I are illustrated by the following representative examples of Scheme 1 in which, unless otherwise stated, R$^1$, R$^2$, R$^3$, R$^4$, R$^5$, Z, and A have the significance given herein before and R' and R" independently represent hydrogen, an optionally substituted aryl or an optionally substituted amino group.

Scheme 1

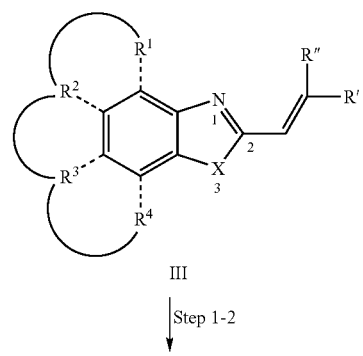

III

Step 1-2

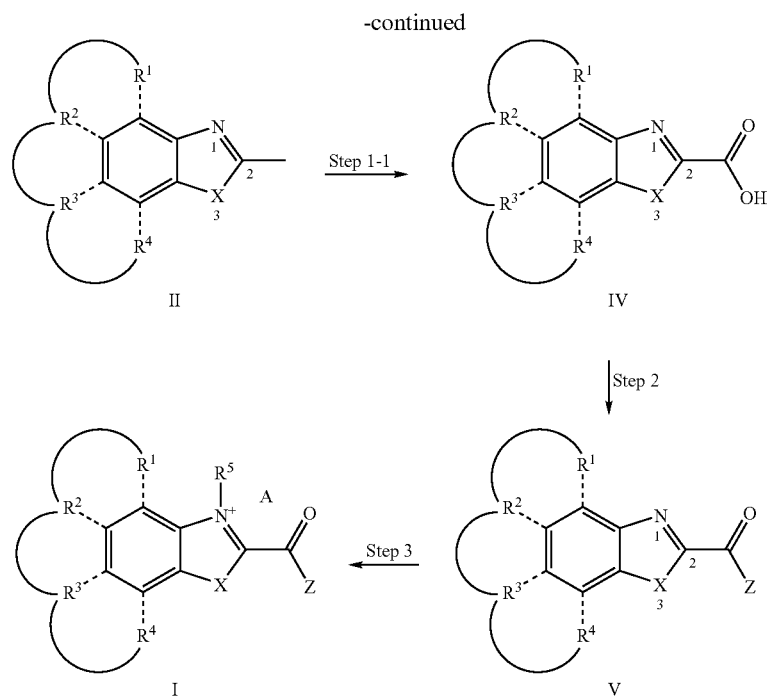

A preferred method for the synthesis of the compounds of Formula I starts from the corresponding 2-methyl derivatives of Formula II.

The necessary starting compounds of Formula II are commercially available or may be obtained by standard procedures of organic chemistry:

For X representing —$CR^6R^7$—, wherein $R^6$ and $R^7$ have the meaning given hereinbefore, the 2-methyl derivatives of Formula II can be prepared by an Fischer-type reaction starting from the corresponding naphtylhydrazides (which are obtainable from the corresponding amines by diazotation and reduction, e.g., with $SnCl_2$) and a ketone $CH_3$—C(O)—$CR^6R^7$ (e.g. 3-methyl-2-butanone, 3-methyl-2-pentanone or 1-cyclohexyl-ethanone and the like). Typically the reaction is carried out in solvents like acetic acid (AcOH), water, ethanol (EtOH) or mixtures thereof in the presence of sodium or potassium acetate (Hughes, D. L., Organic Preparations and Procedures International 25 (1993) 607-632; Zimmermann, T., J. Heterocycl. Chem. 39 (2002) 255-262) Several (Lewis) acids (e.g. $BF_3$-$Et_2O$, HCl/$H_2SO_4$, perchloric or oxalic acid in EtOH, p-toluene sulfonic acid and the like) can be used for catalyzing the cyclisation reaction. Alternatively starting from the corresponding naphtol derivatives, which are reacted with a ketone $CH_3$—C(O)—$CR^6R^7$ in the presence of hydrazine and catalytic amounts of methyl sulfonic acid (or other Lewis acids) at high temperatures (e.g. boiling xylene), the compounds of Formula II (EP 0 790 238) are prepared. Furthermore naphtylbromides can be converted to the 2-methyl derivatives of Formula II in two steps via a palladium catalyzed Buchwald-Hartwig type reaction with e.g. diphenylmethylhydrazine (which yields the corresponding naphtylhydrazine) and subsequent condensation with a ketone $CH_3$—C(O)—$CR^6R^7$ in the presence of catalytic amounts of p-toluene sulfonic acid.

For X representing —S—, the 2-methyl derivatives of Formula II can be prepared by a cyclisation starting from the corresponding N-naphtyl thioacetamides (obtainable from the corresponding naphtylamines) which are reacted in aqueous or alcoholic alkali (eventually in the presence of $K_3FeCN_6$). Another possibility starts from 1,2-diphenylethanones or respectively from their α-bromo-derivatives which are condensed with thioacetamide to 2-methyl-4,5-diphenyl-thiazoles. These intermediates can be converted in an oxidative coupling reaction (e.g. Moreno, I., et al., European J. Org. Chem. 13 (2002) 2126-2135) to 2-methyl-phenanthro[9,10-d]thiazole derivatives of Formula II.

For X representing —O— the 2-methyl derivatives of Formula II can be prepared from the corresponding (acetylated) o-aminonaphtol derivatives by a cyclization reaction under acidic catalysis (eventually in the presence of AcOH/acetic anhydride or under pressure) at temperatures between 60 and 150° C.

For X representing —$NR^6$—, wherein $R^6$ has the meaning given hereinbefore, the 2-methyl derivatives of Formula II can be prepared from the corresponding (acetylated) o-diaminonaphtalene derivatives by a cyclization reaction under acidic catalysis (eventually in the presence of AcOH/acetic anhydride or under pressure) at temperatures between 60 and 150° C.

The alkene derivatives of Formula III are either commercially available or they can be prepared for example from the methyl derivatives of Formula II in a condensation reaction with aromatic aldehydes usually under basic (sometimes acidic) conditions. The enamine derivatives of Formula III are obtainable by the reaction of compounds of Formula II with N,N-dimethylformamide dimethyl acetal in N,N-dimethylformamide (Vetelino, M. G., et al., Tetrahedron Letters 35 (1994) 219-222) or with aromatic nitriles in the presence of lithium organic compounds (e.g. BuLi, PhLi and the like) (Langer, P., et al., European J. Org. Chem. 4 (2002) 686-691, Langer, P., et al., Chemistry 7 (2001) 2617-2627).

Step 1-1 of the reaction sequence (scheme 1) is an oxidation reaction which can be performed in one ore two stages. Direct oxidation of the methyl derivatives of Formula II to carboxylic acid derivatives of Formula III can be achieved by oxidation reagents like potassium permanganate or chromic acid. Alternatively the methyl derivatives of Formula II are first converted into their corresponding aldehydes with $SeO_2$, $CrO_2Cl_2$, $CrO_3/Ac_2O$, ceric ammonium nitrate and the like. Subsequently such aldehydes can be oxidized to carboxylic acid derivatives of Formula IV using silver (I) oxide, potassium permanganate, chromic acid, hydrogen peroxide or other suitable oxidizing reagents. Another two step procedure leads via the 2-dibromomethyl derivatives (yielded by a heteroallylic bromination with NBS under irradiation) to the desired carboxylic acids of Formula IV by the subsequent oxidative hydrolysis with $Ag_2O$ in aqueous sodium hydroxide.

In Step 1-2 of reaction scheme 1, the carboxylic acids of Formula IV are obtainable by an oxidative cleavage reaction from the derivatives of Formula III wherein R' and R" independently represent hydrogen, an optionally substituted aryl or an optionally substituted amino group. Such oxidative cleavage can be performed in the presence of $NaIO_4$, potassium permanganate or ozone (ozonolysis) and leads to aldehyde intermediates (Vetelino, M. G., et al., Tetrahedron Letters 35 (1994) 219-222) which can be oxidized (eventually without isolation) to carboxylic acids of Formula III as described above for the second stage of Step 1-1.

In Step 2 of the reaction scheme 1 the leaving group Z is introduced. This reaction is normally carried out in a two step procedure.

In the first step, the carboxylic acid of the Formula IV becomes activated. This reaction is carried out in an inert solvent or diluent, for example, in dichloromethane, dioxane, tetrahydrofuran (THF) or N,N-dimethylformamide (DMF) in the presence of an activating agent. Suitable activating agents are, for example, oxalyl or thionyl chloride, isobutyl chloroformate, N-hydroxybenzotriazole, N,N'-carbonyldiimidazole, dicyclohexylcarbodiimide, N-(3-dimethylaminopropyl)-N'-ethylcarbodiimide (EDC), 2-morpholino-ethyl-isocyanide (MEI) and the like. Other activating agents can also be used and are well known to the skilled artist. The activated carboxylic acid derivative (e.g. the acid chloride) can be sometimes isolated as intermediate. Nevertheless the reaction is often carried out in a one-pot procedure without isolation of the activated carboxlic acid intermediate.

In the second step, the leaving group Z is introduced by adding Z (e.g. as a solution of its anion formed by reaction with a non-nucleophilic base like e.g. sodium hydride, triethylamine or diisopropylethylamine) to the activated carboxylic acid yielding the compounds of Formula V. This reaction can be catalyzed sometimes by N,N-dimethylaminopyridine (DMAP) and the like. These methods are well known to those skilled in the art and depending of the nature of the leaving group Z different activation reactions may be suitable.

The leaving group Z might bear an suitable protecting group e.g. for an carboxylic acid moiety which can be comprised in Z. Such protecting groups can be e.g. t-butyl, t-butyl-dimethyl-silyl, benzyl, ethyl or other appropriate protecting groups known in the art. After the introduction of Z, such protecting groups can be cleaved to release e.g. a free carboxylic acid moiety. Such carboxylic acid moiety can then be converted into coupling moiety e.g. N-succinimidyl-oxycarbonyl by activating the carboxylic acid and reacting the activated acid intermediate with N-hydroxysuccinimide (HOSu). Also other coupling moieties can be introduced in such a carboxylic acid group. And furthermore other protected functional groups like acylated or silylated amino groups can be present in Z.

The cleavage of a protecting group in Z and/or the introduction of an optional coupling moiety in Z is either performed after Step 2 (Introduction of the leaving group Z). Or alternatively the cleavage of the protecting group in Z as well as the introduction of the optional coupling moiety in Z is carried out after Step 3 (N-alkylation).

Step 3 of the reaction sequence (scheme 1) is an N-alkylation of the nitrogen of the 1-position of compounds of Formula V. For the N-alkylation different methods are known. Conventionally compounds of Formula V are reacted with alkyl halides, especially alkyl iodides or bromides (e.g. MeI, EtI, EtBr and the like) or with trifluoromethyl-, methyl- or p-toluolene-sulfonates (e.g. MeOTf) to afford the corresponding compounds of Formula I. Alternatively tetralkyl boronium salts (e.g. $Me_4B^+$, $BF_4^-$) can be used. The counterion A, which depends on the alkylating reagent used, can be exchanged by known methods so that for example the solubility of compounds of Formula I can be altered.

For the introduction of sulfoalkyl groups at the 1-position of compounds of Formula V, usually the corresponding sultone (cyclic alkylsulfonate) is used as alkylating agent (Flanagan, J. H., et al., Bioconjugate Chem. 8 (1997) 751-756; Adamczyk, M., et al., J. Org. Chem. 63 (1998) 5636-5639). Lewis acids (e.g. $BF_3$-$Et_2O$) can higher the yields (U.S. Pat. No. 5,326,876). Alternatively the sulfopropylation can be preformed with the more reactive O-protected neopentyl 3-triflyloxypropanesulfonate (Adamczyk M., et al., J. Org Chem. 63 (1998) 5636-5639), wherein the neopentyl protecting group is cleaved after alkylation to release the free sulfo group.

The intermediates of Formula IV and V are also subject of the present invention.

According to the reaction scheme 1 above the following substances can be prepared and are also an embodiment of the invention:

2-[4-(N-Succinimidyl-oxycarbonyl)-2,6-dimethyl-phenoxycarbonyl]-1,1-dimethyl-3-(3-sulfopropyl)-1H-benzo[e]indolium Inner Salt;

2-[4-(N-Succinimidyl-oxycarbonyl)-2,6-dimethyl-phenoxycarbonyl]-1,1-dimethyl-3-(4-sulfobutyl)-1H-benzo[e]indolium Inner Salt;

2-(3-Chlorosulfonyl-2,6-dimethyl-phenoxycarbonyl)-1,1,3-trimethyl-1H-benzo[e]indolium triflate (iodide or bromide);

2-(3-Chlorosulfonyl-2,6-dimethyl-phenoxycarbonyl)-1,1-dimethyl-3-(3-sulfopropyl)-1H-benzo[e]indolium Inner Salt;

2-{4-[3-(N-Succinimidyl-oxycarbonyl)-propyl]-benzenesulfonyl}-(3-sulfo-propyl)-aminocarbonyl)-1,1,3-trimethyl-1H-benzo[e]indolium Inner Salt; and 2-{4-[3-(N-Succinimidyl-oxycarbonyl)-propyl]-benzenesulfonyl}-(3-sulfo-propyl)-aminocarbonyl)-3-ethyl-1,1-dimethyl-1H-benzo[e]indolium Inner Salt;

and especially

2-{4-[3-(N-Succinimidyl-oxycarbonyl)-propyl]-benzenesulfonyl}-(3-sulfo-propyl)-aminocarbonyl)-1,1-dimethyl-3-(3 -sulfopropyl)-1H-benzo[e]indolium Inner Salt; and 2-{4-[3-(N-Succinimidyl-oxycarbonyl)-propyl]-benzenesulfonyl}-(3-sulfo-propyl)-aminocarbonyl)-1,1-dimethyl-3-(4-sulfobutyl)-1H-benzo[e]indolium Inner Salt.

Furtheron the following substances can be prepared according to scheme 1 and are also an embodiment of the invention:

2-[4-(N-Succinimidyl-oxycarbonyl)-2,6-dimethyl-phenoxy-carbonyl]-3,3-dimethyl-1-(3-sulfopropyl)-3H-benzo[g]indolium Inner Salt;
2-[4-(N-Succinimidyl-oxycarbonyl)-2,6-dimethyl-phenoxy-carbonyl]-3,3-dimethyl-1-(4-sulfobutyl)-3H-benzo[g]indolium Inner Salt;
2-(3-Chlorosulfonyl-2,6-dimethyl-phenoxycarbonyl)-1,3,3-trimethyl-3H-benzo[g]indolium triflate (iodide or bromide); and
2-(3-Chlorosulfonyl-2,6-dimethyl-phenoxycarbonyl)-3,3-dimethyl-1-(3-sulfopropyl)-3H-benzo[g]indolium Inner Salt;

and especially
2-{4-[3-(N-Succinimidyl-oxycarbonyl)-propyl]-benzene-sulfonyl}-(3-sulfo-propyl)-aminocarbonyl)-1,3,3-trim-ethyl-3H-benzo[g]indolium triflate (iodide or bromide);
2-{4-[3-(N-Succinimidyl-oxycarbonyl)-propyl]-benzene-sulfonyl}-(3-sulfo-propyl)-aminocarbonyl)-1-ethyl-3,3-dimethyl-3H-benzo[g]indolium triflate (iodide or bromide);
2-{4-[3-(N-Succinimidyl-oxycarbonyl)-propyl]-benzene-sulfonyl}-(3-sulfo-propyl)-aminocarbonyl)-3,3-dimethyl-1-(3-sulfopropyl)-3H-benzo[g]indolium Inner Salt; and
2-{4-[3-(N-Succinimidyl-oxycarbonyl)-propyl]-benzene-sulfonyl}-(3-sulfo-propyl)-aminocarbonyl)-3,3-dimethyl-1-(4-sulfobutyl)-3H-benzo[g]indolium Inner Salt.

Furtheron the following substances can be prepared according to scheme 1 and are also an embodiment of the invention:
1,1-dimethyl-3-(3-sulfopropyl)-2-(2,4,6-trichloro-phenoxy-carbonyl)-1H-benzo [e]indolium Inner salt;
1,1-dimethyl-3-(4-sulfobutyl)-2-(2,4,6-trichloro-phenoxy-carbonyl)-1H-benzo[e]indolium Inner salt; and
1,1,3-Trimethyl-2-(2,4,6-trichloro-phenoxycarbonyl)-1H-benzo[e]indolium triflate (iodide or bromide).

The present invention represent very attractive labels, e.g., for labeling of biomolecules. The methods used for coupling of labels to biomolecules have significantly matured during the past years and an excellent overview is given in Aslam, M., and Dent, A., Bioconjugation (1998) 216-363, London, and in the chapter "Macromolecule conjugation" in Tijssen, "Practice and theory of enzyme immunoassays" (1990), Elsevier, Amsterdam.

Appropriate coupling chemistries are known from the above cited literature (Aslam, supra). The chemical compound according to the present invention preferably is designed and synthesized to comprise a coupling group or coupling moiety which matches the coupling chemistry appropriate for the biomolecule under investigation.

In a preferred embodiment the chemical compound according to the present invention comprises only one coupling moiety within $R^5$, $R^6$, $R^7$ or $R^{10}$. Preferably the coupling moiety is part of $R^5$ or $R^{10}$. More preferred the coupling moiety is part of $R^{10}$.

The coupling moiety is a reactive group or activated group which is used for chemically coupling of the compound to a biomolecule. As the skilled artisan will appreciate the coupling moiety is selected to match the chemical function on the biomolecule to which coupling shall be performed.

The chemiluminescent compounds of the present invention, depending on which coupling moiety is selected, can be reacted directly with the biomolecule either in an aqueous or an organic medium.

The chemiluminescent labels can be either directly attached to the biomolecule or connected to the biomolecule via a spacer to form a chemiluminescent conjugate comprising the biomolecule and a compound of the present invention. An example of preparing an Anti-TSH conjugate (i.e., a conjugate comprising an antibody to TSH and a compound according to Formula I) is provided in the examples section.

Amino groups of biomolecules (the terminal —$NH_2$ group or the $NH_2$ group of a lysine side chain, as well as ω-amino groups of diamino carboxylic acids) can be used for chemical coupling of a marker group thereto based on "amino chemistry". Well-known examples of amino chemistry comprise amongst others the reaction of amino groups with so-called activated groups, like NHS-esters, other activated esters, acid chlorides and azides.

Carboxyl groups on biomolecules (the terminal $COO^-$-group, the carboxy functions of glutamic acid or aspartic acid) are used for chemical coupling based on "carboxy chemistry". Well-known examples of carboxy chemistry comprise amongst others the activation of these of carboxy groups to carry the above mentioned activated groups. Coupling to e.g., amino groups on the marker is then easily performed.

Alternatively sulfhydryl groups on biomolecules (e.g. free-SH-groups of cysteine or —SH groups obtained by reducing di-sulfhydryl bridges) are used for chemical coupling based on "sulfhydryl chemistry". Well-known examples of sulfhydryl chemistry comprise amongst others the reaction of —SH groups with maleimido groups, or alkylation with α-halogen carboxylic group or by thioethers.

The hydroxyl group of tyrosine residues or the imidazole group of histidine also may be used to covalent link compounds according to the present invention to a biomolecule by aid, e.g., of diazonium groups.

The coupling moiety may be either part of the chemiluminescent heterocycle of Formula I or of the leaving group. It is generally accepted that large biomolecules may interfere with the luminescent light emitted by the chemiluminescent group if both the chemiluminescent group and biomolecule are in close proximity. It is therefore preferred that the coupling group is part of the leaving group and to preferably use such compound for coupling to a biomolecule. In the case such a conjugate is used in a chemiluminescence assay upon release of the chemiluminescent heterocycle from the biomolecule to which the leaving group remains attached, both molecules the luminophore and the biomolecule no longer are in close proximity. This is advantageous in an assay for detection of an analyte in a sample.

The term "biomolecule" comprises molecules and substances of interest in a therapeutic or a diagnostic field. Biomolecule in the sense of the present invention is any naturally occurring or synthetically produced molecule composed of amino acids, nucleotides, nucleosides, lipids, hormones and/or sugars. As the skilled artisan will appreciate non-naturally occurring derivatives e.g., of amino acids, or nucleotides, like artificial amino acids or artificial nucleotides or nucleic acid analogs may also be comprised in a biomolecule without departing from the spirit of this invention.

In a preferred embodiment the biomolecule is selected from the group consisting of polypeptides, nucleic acids, and low molecular weight drugs. Wherein low molecular weight is a molecular weight below 5000 Da.

Especially preferred are biomolecules which function as a specific binding partner for a biological, biochemical or chemical species.

A conjugate between a biomolecule and a chemiluminescent compound according to the present invention, represents a further preferred embodiment. It will be readily appreciated by the skilled artisan that conjugates between a biomolecule and the chemical compounds described in the present invention are of great advantage, e.g., in a specific binding assay for detection of an analyte in a sample.

It is especially preferred to use a compound according to the present invention or a biomolecule-conjugate comprising such compound in an assay employing chemiluminescence detection. Preferably such chemiluminescence based assay is a specific binding assay, e.g. an immuno assay.

Specific binding assays in general are based on the specific interaction of two members of a bioaffine binding pair. Examples of preferred specific binding partners in such binding pairs are hapten or antigen and an antibody reactive thereto, biotin or biotin-analogs such as aminobiotin, iminobiotin, or desthiobiotin which binds to biotin or streptavidin, sugar and lectin nucleic acid or nucleic acid analogs and complementary nucleic acid, receptor and ligand for example steroid hormone receptor and steroid hormone, and enzymes and their substrates.

The specific interaction between nucleic acids (or nucleic acid analogs) and nucleic acids complementary thereto in assays based on detection of hybridization between nucleic acid stands and the specific interaction of antibodies with their respective antigen on which the broad range of immunoassays is based, are most relevant in diagnostic routine.

The theory and practice of nucleic acids hybridization assays is summarized in relevant text books, like Kessler, C., "Non-radioactive labeling and detection of biomolecules", Springer Verlag, Berlin Heidelberg (1992). The skilled artisan will find all relevant details therein.

Immunoassays nowadays are broadly used and general knowledge to the skilled artisan. Relevant methods and procedures are summarized in related text books, like Aslam, M., and Dent, A., Bioconjugation (1998) 216-363, London, and Tijssen, "Practice and theory of enzyme immunoassays" (1990), Amsterdam, Elsevier. A comprehensive review can also be found in an article authored by Mayer, A., and Neuenhofer, S., Angewandte Chem. Intern. Ed. Engl. (1994) 1063-1068, Weinheim, VCH Verlagsgesellschaft mbH.

In a further preferred embodiment the present invention relates to a method of performing a chemiluminescence assay based on the use of a compound according to the present invention.

Such chemiluminescence based assaymethod is characterized in that in the presence of trigger solution luminescent light is emitted and can be measured.

Figure 2:
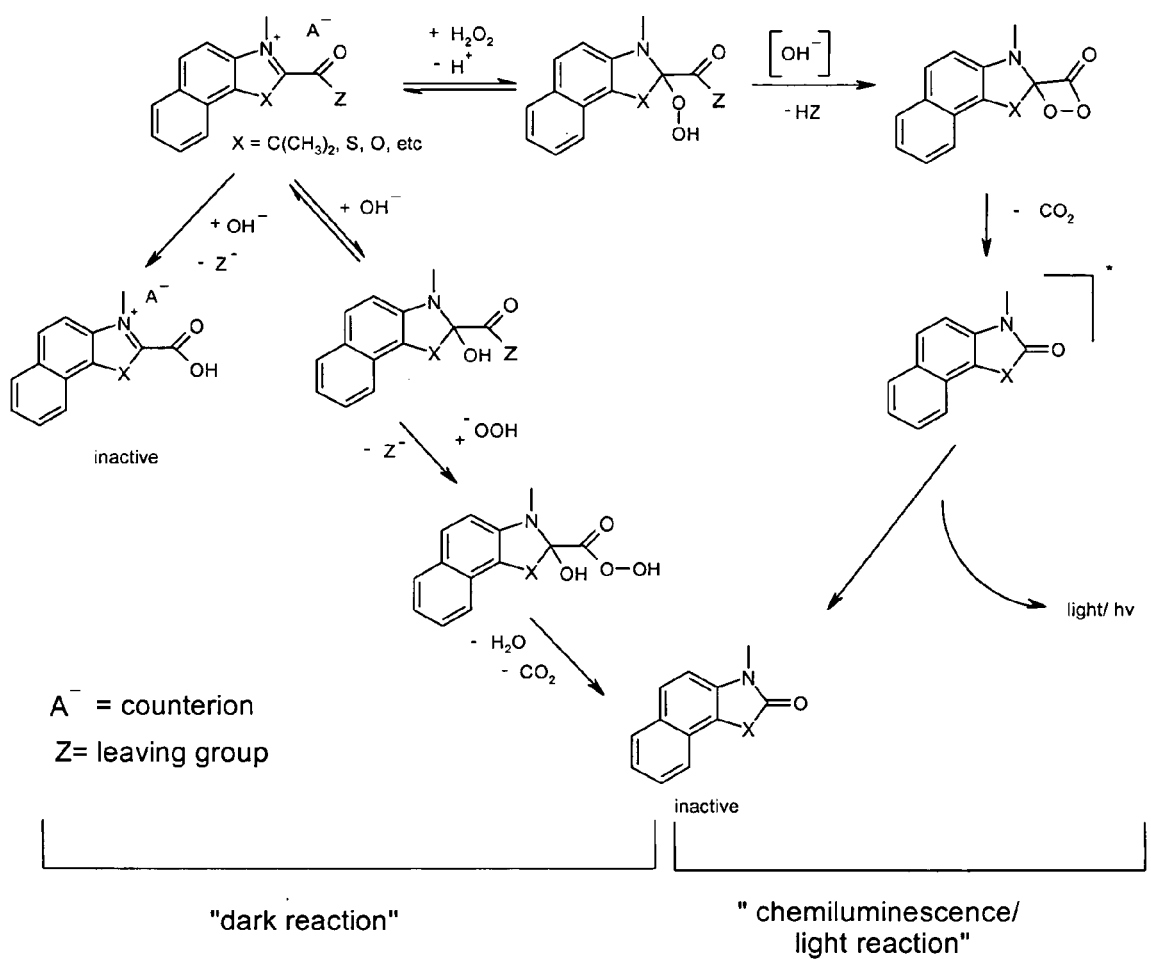
FIG. 2: Mechanism of chemiluminescence for a compound according to Formula I This schematic represents the likely mechanisms on which chemiluminescence of a compound according to Formula I can be based.
Figure 3:
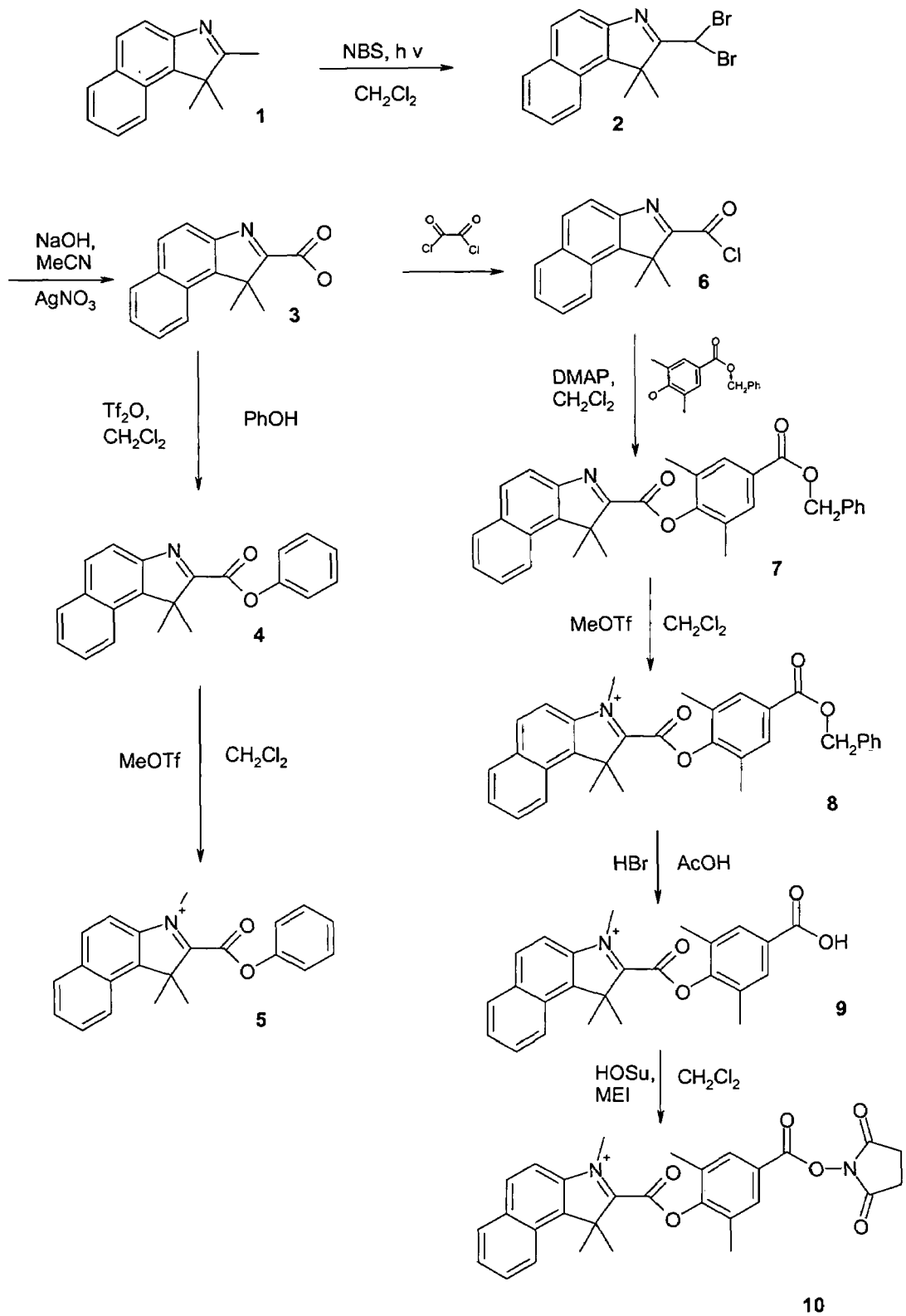
FIG. 3: Synthesis of dimethyl-benzindolium carboxylic acid active ester This schematic represents the synthesis pathway as detailed in Examples 1 and 2.

Upon the action of a trigger solution, e.g., peroxide or a reactive oxygen species like the oxygen radical anion the chemiluminescent compound of the present invention most likely according to the mechanism illustrated in FIG. 2 forms a dioxetane intermediate which is decarboxylated to generate an electronically excited emitter. The transition to the ground state of this emitter ensues by emission of a photon (=chemiluminescence). The energy (light) which is thereby emitted is measured according to standard procedures and with routine equipment.

As indicated, $H_2O_2$ or a reactive oxygen species like the oxygen radical anion has to be present to form the intermediate dioxetanone. $H_2O_2$ can be added directly or generated indirectly e.g. by enzymatic reaction (glucose oxidase/glucose). Reactive oxygen species are generated during the chemiluminescent reaction from oxygen or $H_2O_2$. Alternatively, a reactive oxygen species can be generated intentionally e.g. by the oxygen initiated C—C coupling (indoxyl-phosphate, U.S. Pat. No. 5,589,328).

Of course the oxidation conditions, i.e., the trigger solution must be chosen such that no destruction of the light emitting molecule occurs and a maximum of light emission is achieved. Trigger solutions may be set up as a single mixture of trigger reagents or triggering may be based on two separate trigger solutions which if combined trigger chemiluminescence. Trigger solutions in the later case for example are 0.5% $H_2O_2$, 0.1 M $HNO_3$ for trigger 1 and 0.25 M NaOH and 0.125% Cetyl trimethyl ammonium chloride (CTAC) for trigger 2.

The generation of the chemiluminescence signal may be accelerated or increased by the use of mediators or enhancers.

Mediators are redox-active compounds which facilitate the oxidation of a compound by accelerating electron transfer processes. The mediator is oxidized by the oxidant and oxidizes then the compounds according to the invention, whereby the mediator is reduced again. Typical mediators are hexocyanoferrate (II) and metal complexes like ferrocene. Other enhancers which are used in chemiluminescence reactions include chemicals like iodo-phenol or phenyl boronic acid.

The oxidation preferably is performed in the presence of an appropriate detergent, which creates a hydrophobic microenvironment around the light emitting heterocyclic ketone. This results in an increase of the chemiluminescence quantum yield since quenching due to interaction with water molecules is reduced. Additionally an appropriate fluorophore, like fluorescein can be attached covalent to the detergent or alternatively a fluorophore can be added to the reaction mixture in order to facilitate an energy transfer from the excited heterocyclic ketone to this fluorophore.

The present invention also relates to a method for synthesizing a compound of Formula I. Preferably such synthesis comprises the steps of generating a carboxyl moiety at position 2 of the heterocycle according to general Formula II, e.g., by oxidation of the 2-methyl group and subsequent activation of this moiety e.g by halogenation or in situ by dicyclohexylcarbodiimide (DCC) or similar reagents.

Formula II:

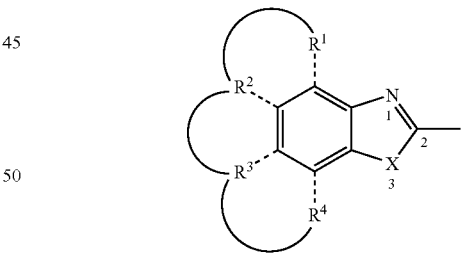

wherein $R^1$ to $R^4$ and X are as defined above for Formula I.

Then the leaving group Z is introduced in a dry organic solvent eventually supported by adding a non-nucleophilic base, i.e. pyridine, dimethylaminopyridine (DMAP) and the like. Finally the nitrogen of the heterocyclic ring system at position 1 is alkylated by e.g., methyltriflate, propanesultone or other alkylating reagents.

The following examples, references, and figures are provided to aid the understanding of the present invention, the true scope of which is set forth in the appended claims. It is understood that modifications can be made in the procedures set forth without departing from the spirit of the invention.

EXAMPLE 1

Synthesis of Dimethyl-benzindolium Carboxylic Acid Active Ester 5 a) Synthesis of 2-Dibromomethyl-1,1-dimethyl-1H-benzo[e]indole 2

2.0 g (9.56 mmol) 2,1,1-Trimethyl-1H-benzo[e]indole 1, 5.1 g (28.66 mmol) N-bromo-succinimide and 0.25 g of AIBN were dissolved in 200 mL methylene chloride. This reaction mixture was irradiated with UV light and refluxed for 5 hours. Then 50 g of silica gel were added and the solvent was removed under reduced pressure. The silica was loaded on a gravity column and eluted with petrolether/ethyl acetate (with a gradient from 20% to 33% ethyl acetate). The appropriate fractions were combined and evaporated under reduced pressure to yield 3.5 g of product 2 as a pale yellow foam.

MS: ESI: $M^+$=366.86; $R_f$(petrolether/EtOAc 3:1)=0.66 b) Synthesis of 1,1-dimethyl-1H-benzo[e]indole-2-carboxylic acid 3

To a solution of 3.5 g (9.5 mmol) Dibromomethyl-1,1-dimethyl-1H-benzo[e]indole 2 in 200 mL acetonitrile successively 28.5 mL 1N NaOH and 4.84 g (28.5 mmol) silver nitrate were added. The reaction mixture was stirred for 1.5 hours at room temperature and then filtered over a pad of celite. The filtrate was diluted with 800 mL ethyl acetate and washed once with 400 mL brine. The aqueous phase was re-extracted three times with ethyl acetate and all organic extracts were combined and dried over magnesium sulfate. After evaporation of the solvent the orange residue was triturated with 200 mL petrolether/diethylether 1:1 to give a pale yellow solid, which was filtered off and purified by column chromatography on silica gel (eluent: MeCN/MeOH; 5% to 25% MeOH). The fractions containing the desired product were collected and the solution was evaporated under reduced pressure to give 1.0 g of 3 as pale yellow solid.

MS: ESI: $M^+$=238.96; $R_f$(MeCN/MeOH 4:1)=0.23 c) Synthesis of Phenyl-1,1-dimethyl-1H-benzo[e]indole-2-carboxylate 4

200 mg of 1,1-dimethyl-1H-benzo[e]indole-2-carboxylic acid 3 (0.84 mmol) and 395 mg (4.2 mmol) phenol were dissolved in 50 mL methylene chloride. Then 188 µL (1.12 mmol) trifluorosulfonic acid anhydride were added and the reaction mixture was stirred at room temperature for 5 hours. After evaporation of the solvent under reduced pressure, the residue was taken up in methylene chloride and washed with 0.1 N NaOH and water. The organic phase was separated, dried over sodium sulfate and filtered. The solvent was removed under vacuum and the crude product was purified by preparative HPLC column chromatography (eluent: water-acetonitrile). The appropriate fractions were combined and dried by lyophilization to yield 7.5 mg of product 4.

MS: ESI: $M^+$=315.01; Rf(diethylether/hexane 1:1)=0.57 d) Synthesis of 1,1,3-Trimethyl-2-phenoxycarbonyl-1H-benzo[e]indolium trifluoromethanesulfonate 5

To a solution of 7.5 mg (0.024 mmol) of 4 in 3 mL methylene chloride were added slowly under stirring 7.8 µL (0.071 mmol) methyl triflate. After 3 hours at ambient temperature the starting material was used up (TLC) and product 5 was precipitated by addition of 7 mL diethylether/hexane 1:1. The red solid was filtered and dried under vacuum to yield 4.5 mg of 5.

MS: ESI: $M^+$=330.11; $R_f$(diethylether/hexane 1:1)=0.40; $^1$H-NMR (CDCl$_3$, 300 MHz): δ(ppm)=2.18 (s, 6H); 4.73 (s, 3H); 7.49 (m, 5H); 7.82 (m, 3H); 8.15 (m, 3H).

EXAMPLE 2

Synthesis of Dimethyl-benzindolium Carboxylic Acid Active Ester 10 a) Synthesis of 1,1-dimethyl-1H-benzo[e]indole-2-carboxylic acid chloride 6

100 mg 1,1-dimethyl-1H-benzo[e]indole-2-carboxylic acid 3 (see under Example 1) were dissolved in 1.6 mL oxalyl chloride under vigorous developement of HCl-gas. While the solution was stirred at ambient temperature slowly a bright yellow began to precipitate. After 1.5 hours the reaction was complete and the excess of oxalylchloride was removed by distillation to give a yellow solid which was used without further purification.

b) Synthesis of (4-Benzyloxycarbonyl-2,6-dimethyl)-phenyl-1,1-dimethyl-1H-benzo[e]indole-2-carboxylate 7

100 mg of 1,1-dimethyl-1H-benzo[e]indole-2-carboxylic acid chloride 6 (0.386 mmol) and 125 mg (0.486 mmol) 4-Benzyloxycarbonyl-2,6-dimethylphenol were dissolved in 5 mL methylene chloride and 60 mg (0.486 mmol) of 4-dimethylaminopyridine (DMAP) were added. The reaction mixture was stirred at room temperature for 3 hours and subsequently diluted with 50 mL ethylacetate. After extraction with solutions of sodium bicarbonate, 0.1N HCl and brine the organic phase was separated, dried over magnesium sulfate and filtered. The organic solution was concentrated and the crude product was purified by column chromatography on silica gel, eluting with diethylether/hexane 2:1, to give 20 mg of 7 as a pale yellow solid.

MS: ESI: $M^+$=477.15; $R_f$(diethylether/hexane 2:1)=0.19 c) Synthesis of (4-Benzyloxycarbonyl-2,6-dimethyl)-phenyl-1,1,2-trimethyl-1H-benzo[e]indolium-2-carboxylate trifluoromethanesulfonate 8

To a solution of 20 mg (0.051 mmol) (4-Benzyloxycarbonyl-2,6-dimethyl)-phenyl-1,1-dimethyl-1H-benzo[e]indole-2-carboxylate 7 in 3 mL methylene chloride was added methyl triflate (17 µL; 0.153 mmol) and the mixture was stirred at room temperature for 20 hours. The reaction mixture was treated subsequently with petrolether/diethylether 1:2 whereupon a yellow precipitate was formed. The yellow solid was filtered, washed several times with petrolether/diethylether 1:2, and then dried to give 21 mg of 8.

MS: ESI: $M^+$=492.16; $R_f$(diethylether)=0.72 d) Synthesis of (4-Carboxy-2,6-dimethyl)-phenyl-1,1,2-trimethyl-1H-benzo[e]indolium-2-carboxylate trifluoromethanesulfonate 9

A mixture of 20 mg (0.041 mmol) (4-Benzyloxycarbonyl-2,6-dimethyl)phenyl-1,1-dimethyl-1H-benzo[e]indole-2-carboxylate 8 in 1.0 mL chloroform was treated with a solution of 30% HBr in acetic acid (2.0 mL) and the reaction mixture was stirred at 50° C. for 1 hour. The solution was diluted with 30 mL of ethyl acetate and washed with brine. Then the organic phase was dried over magnesium sulfate, filtered and concentrated to yield 18 mg of 9 as a yellow solid. This crude product was used without further purification.

MS: ESI: M$^+$=402.06 e) Synthesis of 2-[4-(N-Succinimidyl-oxycarbonyl)-2,6-dimethyl-phenoxy-carbonyl]-1,1,3-trimethyl-1H-benzo[e]indolium trifluoromethanesulfonate 10

17 mg (0.042 mmol) of (4-Carboxy-2,6-dimethyl)-phenyl-1,1,2-trimethyl-1H-benzo[e]indolium-2-carboxylate trifluoromethanesulfonate 9 and 6.3 mg (0.055 mmol) N-Hydroxysuccinimide (HOSu) were dissolved in 2.0 mL methylene chloride. Then 7.5 µL (0.055 mmol) 2-Morpholino-ethyl-isocyanide (MEI) were added slowly and the mixture was stirred for 16 hours at room temperature. The solvent was removed under reduced pressure and the red oily residue was purified by preparative HPLC column chromatography (eluent: water-acetonitrile).The appropriate fractions were collected and dried by lyophilization to yield 5.6 mg of product 10 as a pale yellow solid.

MS: ESI: M$^+$=499.11; $^1$H-NMR (CDCN, 300 MHz): δ(ppm)=1.96 (s, 6H); 2.31 (s, 6H); 4.00 (bs, 3H); 7.06 (d, 1H, J=8.7 Hz); 7.23 (m, 1H); 7.43 (m, 1H); 7.88 (m, 2H); 7.98 (m, 3H).

EXAMPLE 3

Evaluation of Dimethyl-benzindolium Carboxylic Acid Active Ester 5 (Kinetics, Sensitivity)

Kinetics:

Measurements were performed on a Berthold Lumat LB 953. Two triggers have been used to produce chemiluminescence, both promoting CL-reaction.

Trigger 1: 300 µL; 0.5% $H_2O_2$, 0.1 M $HNO_3$

Trigger2: 300 µL; 0.25 M NaOH, 0.125% Cetyl trimethyl ammonium chloride (CTAC) dimethyl-benzindolium carboxylic acid active ester 5 was diluted to 1×10$^{-9}$ Mol/L in PBS-buffer containing 0.1% Thesit. 100 µL sample was dispensed in a 5 mL Sarsted tube and set into the instrument. Trigger 1 was added in position −1, trigger 2 in the measuring position. Measurement was performed for 10 sec.

Figure 4:
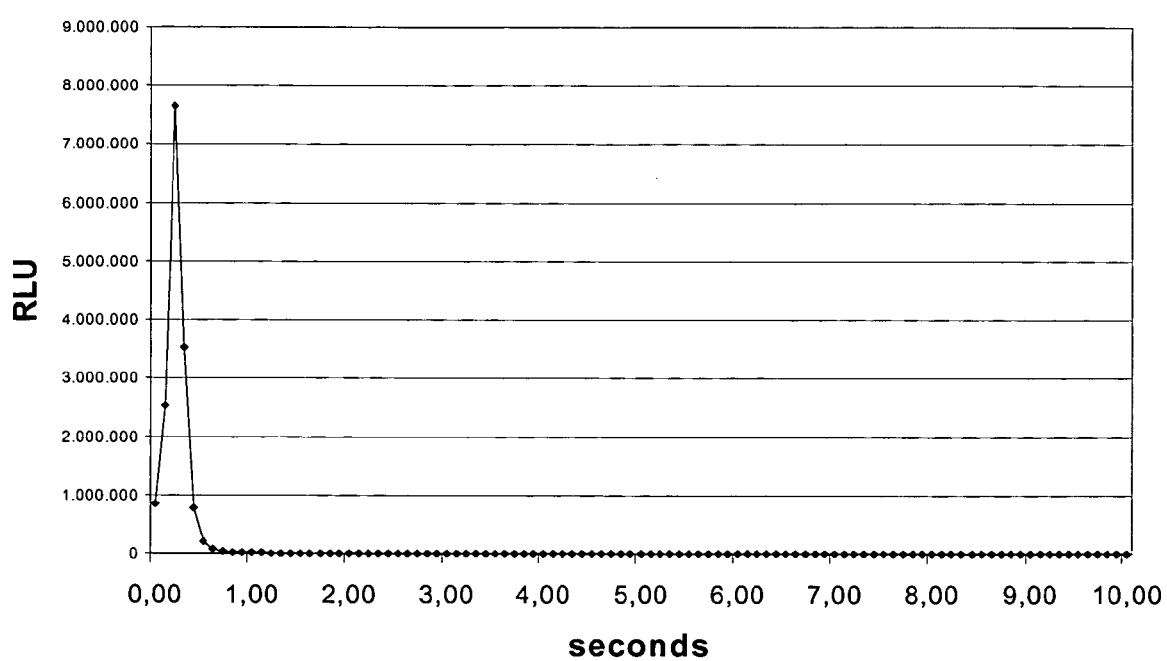
FIG. 4: Chemiluminescence of dimethyl-benzindolium carboxylic acid active ester Shown is the chemiluminescence (in relative light units (RLU)) of dimethyl-benzindolium carboxylic acid active ester. The active ester had been used at a concentration of 1×10E-9 mol/l.

The kinetics of light emission for this compound under the above conditions is shown in FIG. 4.

Sensitivity:

A serial dilution of dimethyl-benzindolium carboxylic acid active ester 5 in PBS-buffer containing 0.1% Thesit was performed. Each sample was measured as described above, except for the measuring time which was only 2 sec. The smallest signal still significantly different from the blank was considered as the lower detection limit.

For comparison, an equivalent serial dilution was made of an acridinium active ester (9-[4-(Succinimidyl-oxycarbonyl-ethyl)-benzenesulfonyl]-(4-methoxy-phenyl)-aminocarbonyl)-10-methyl-acridinium trifluoromethanesulfonate) and measured as described above.

Figure 5:
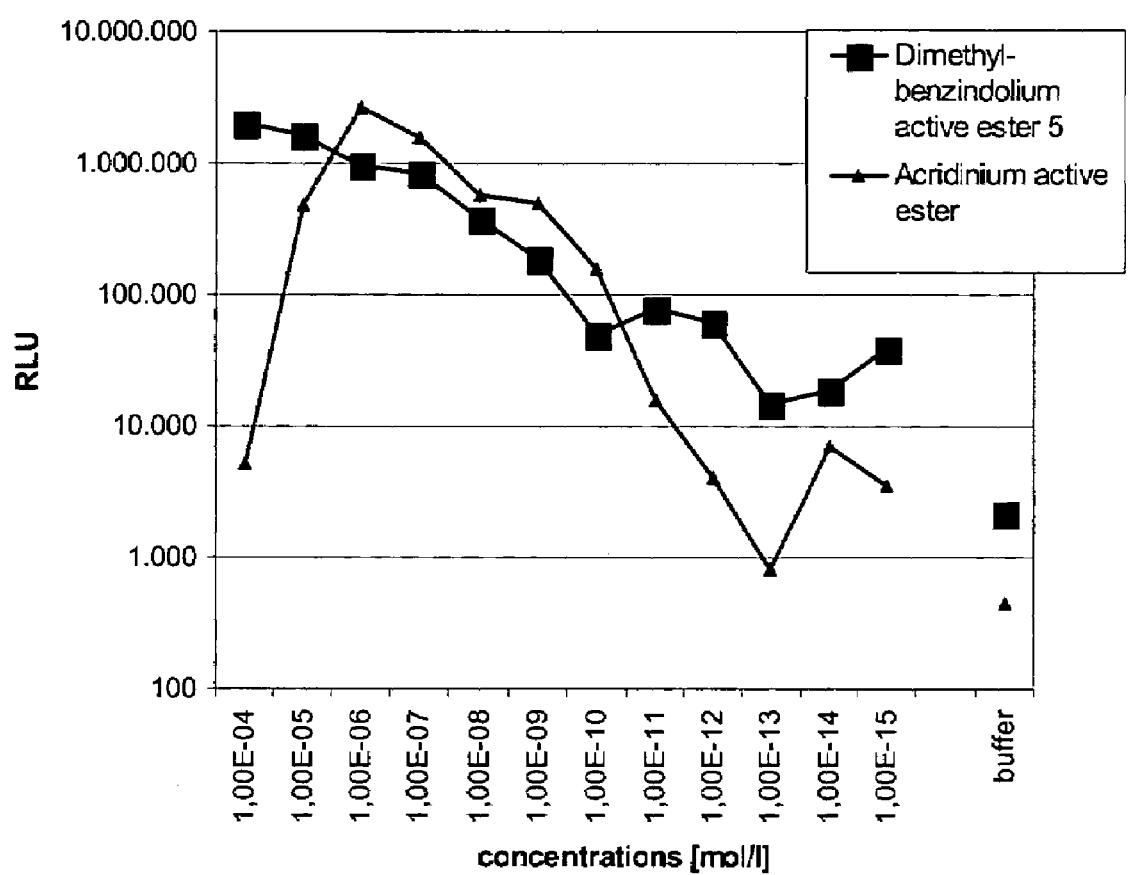
FIG. 5: Sensitivity employing a dimethyl-benzindolium carboxylic acid active ester dimethyl-benzindolium carboxylic acid active ester and the acridinium label 9-[4-(succinimidyl-oxycarbonyl-ethyl)-benzenesulfonyl]-(4-methoxy-phenyl)-aminocarbonyl)-10-methyl-acridinium trifluoromethanesulfonate, which is widely used in diagnostic routine, have been compared. Triangles represent data obtained for dimethyl-benzindolium active ester and squares represent the data obtained with the acridinium active esters.

The results in terms of sensitivity are shown in FIG. 5.

The lower detection limit for dimethyl-benzindolium carboxylic acid active ester according to this invention compares well with the commercially used acridinium label.

EXAMPLE 4

Preparation of an "Anti-TSH Conjugate" Based on Dimethylbenzindolium Carboxylic Acid Active Ester 10 and a Monoclonal Antibody Against TSH A solution of a monoclonal anti-TSH antibody (10 mg; 0.066 µmol) in 1 mL of 0.05 M phosphate buffer, pH 7.8 was treated with a solution of dimethyl-benzindolium carboxylic acid active ester 10 (82 µg; 0.134 µmol) in 50 µL dimethylsulfoxide at room temperature for 1.5 hours. The conjugation was stopped by adding a 10.5 µl of a solution of lysine (1M) in water. Then the pH-value was adjusted with 1M $K_2HPO_4$ to pH 7.8 the conjugate was purified by passing the reaction mixture through a HiLoad 16/60 Superdex 200 pg column packed and eluted with 0.05 M phosphate buffer, pH 6.8. The elution was monitored at 280 nm with an Amersham Pharmacia ÄKTA Explorer UV-900 Detector. The appropriate fractions were collected and dried by lyophilization to yield 6.99 mg of the desired conjugate.

This conjugate has been used in a preliminary assay set-up for the detection of TSH. It has been found that this conjugate is appropriate for detection of TSH in clinical samples.

What is claimed is:

1. A compound having the structure:

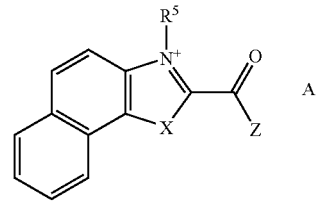

wherein Z is represented by the structure:

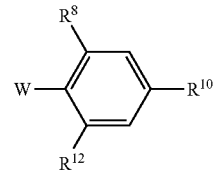

where W is —O—; $R^8$ and $R^{12}$ are independently selected from the group consisting of hydrogen, halogen, alkyl, alkenyl, alkynyl, alkoxy, alkylsulfanyl or alkylamido; and $R^{10}$ is a coupling moiety selected from the group consisting of N-succinimidyl-oxycarbonyl and —$SO_2Cl$;

A represents a counter-ion to balance a net charge of the compound;

X is—$CR^6R^7$ —, and $R^5$, $R^6$ and $R^7$ are independently selected from the group consisting of methyl and ethyl.

2. The compound according to claim 1 wherein $R^6$ and $R^7$ are independently selected from the group consisting of methyl and ethyl groups.

3. The compound according to claim 1 wherein $R^5$ is selected from the group consisting of methyl and ethyl.

4. A method of performing a chemiluminescence assay comprising the steps of: providing a compound according to claim 1, contacting said compound with $H_2O_2$ or a reactive oxygen species, and measuring luminescence emitted from said compound.

5. The method of claim 4 wherein the $H_2O_2$ or a reactive oxygen species is generated by an enzymatic reaction.

6. The method of claim 4 wherein said compound is bound to a specific binding partner, said method further comprising the steps of: contacting a target analyte with said compound to form complexes comprising the compound and the target analyte; separating unbound compounds from said complexes; contacting said complexes with $H_2O_2$ or a reactive oxygen species; and measuring luminescence emitted from said complexes.

7. A method for synthesizing the compound of claim 1, comprising the steps of:

attaching a carboxyl group at position 2 of a compound of the formula:

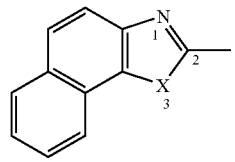

wherein X is as defined in claim 1, introducing a leaving group Z, and alkylating the N-position 1 of the heterocycle.

* * * * *